United States Patent
Barker et al.

(10) Patent No.: US 6,545,173 B1
(45) Date of Patent: Apr. 8, 2003

(54) PROCESS FOR THE PREPARATION OF 1-ARYL-1-CYANOCYCLOBUTANE DERIVATIVES

(75) Inventors: Stephen John Barker, Nottinghamshire (GB); Sharon Michelle Clark, Nottinghamshire (GB)

(73) Assignee: Abbott Laboratories, Abbott Park, IL (US)

(*) Notice: Subject to any disclaimer, the term of this patent is extended or adjusted under 35 U.S.C. 154(b) by 0 days.

(21) Appl. No.: 09/077,698

(22) PCT Filed: Nov. 28, 1996

(86) PCT No.: PCT/EP96/05246

§ 371 (c)(1),
(2), (4) Date: May 28, 1998

(87) PCT Pub. No.: WO97/20810

PCT Pub. Date: Jun. 12, 1997

(30) Foreign Application Priority Data

Dec. 2, 1995 (GB) .............................................. 9524681

(51) Int. Cl.⁷ .......................................... C07C 255/00
(52) U.S. Cl. ..................................................... 558/388
(58) Field of Search .......................................... 558/388

(56) References Cited

U.S. PATENT DOCUMENTS

| 3,526,656 A | 9/1970 | Butler | 260/471 |
| 4,235,926 A | 11/1980 | Holan et al. | 424/282 |
| 4,348,409 A | 9/1982 | Holan et al. | 424/308 |
| 5,405,866 A | 4/1995 | Eliason et al. | 514/436 |

FOREIGN PATENT DOCUMENTS

| AU | 625 414 | 2/1989 |
| EP | 002620 | 6/1979 |
| GB | 1521939 | 8/1978 |
| GB | 1521940 | 8/1978 |
| GB | 2098602 | 11/1982 |
| WO | 93/13073 | 7/1993 |
| WO | 94/26704 | 11/1994 |
| WO | 95/00489 | 1/1995 |

OTHER PUBLICATIONS

Mndzhoyan et al., *Khim.–Farm.ZH.*, 1980, 14(2), p 40–45.
Butler et al., *J. Org. Chem.*, 1971, 36(9), pp. 1308–1309.
Makosza et al., *Rocz. Chem.*, 1966, 40(10), p. 1647–55.
Hill et al., *J. Org. Chem.*, 448, 1993, pp. 9–14.
Case, *J. Am. Chem. Soc.*, 1934, pp. 715–717.
Weber et al., "Phase Transfer Catalysis in Organic Synthesis", Springer Verlag, 1977, pp. 139, 140, 204 and Table 10.1.

Primary Examiner—Joseph K. McKane
Assistant Examiner—Joseph Murray
(74) Attorney, Agent, or Firm—Keil & Weinkauf

(57) ABSTRACT

A process for the preparation of arylcyclobutylnitrile derivatives which involves reaction of a solution of a 1,3-dihalopropane and a cyanobenzyl derivative in a substantialy dimethyl sulphoxide-free solvent with a suspension of a base in a substantially dimethyl sulphoxide-free solvent at a temperature of at least 35° C.

10 Claims, No Drawings

PROCESS FOR THE PREPARATION OF 1-ARYL-1-CYANOCYCLOBUTANE DERIVATIVES

This Application is A 371 of PCT/EP96/05246 filed Nov. 28, 1996.

The present invention relates to an improved process for the preparation of arylcyclobutyl cyanides. 1-(4-Chlorophenyl)cyclobutyl cyanide is an intermediate useful for the preparation of sibutramine, N-1-[1-(4-chlorophenyl) cyclobutyl]-3-methylbutyl-N,N-dimethylamine. Sibutramine is useful in the treatment of depression, Parkinson's disease, obesity, Non Insulin Dependent Diabetes Mellitus (NIDDM) and epilepsy.

The reaction of phenylacetonitrile with a 1,3-dihalopropane in aqueous sodium hydroxide using benzyltriethylammonium chloride as a catalyst to give 1-phenylcyclobutyl cyanide is reported in Rocz. Chem. 40, 1647, (1966). However, the yield is low (26%) and the amount of monoalkylated uncyclised product formed is significant (20%).

1-(4-Chlorophenyl)cyclobutyl cyanide was prepared by reacting 4-chlorophenylacetonitrile with 1,3-dibromobutane in a mixture of dimethyl sulphoxide and ether at 25–35° C. using sodium hydride as the base (J.Org. Chem. 36 (9), 1308, 1971). It is also disclosed that the process is effective if the mineral oil is removed from the sodium hydride by washing with toluene and then adding a slurry of sodium hydride in toluene to the dimethyl sulphoxide. Similar preparations are also described in U.S. Pat. Nos. 4,235,926, 3,526,656, 4,348,409, 5,405,866 and J.Organomet. Chem. 448, 1–2, p9–14(1993). The yields quoted vary between 43% and 78%.

GB2098602A discloses a process for the preparation of 1-(4-chlorophenyl)cyclobutyl cyanide comprising the reaction of 4-chlorophenylacetonitrile with a 1,3-dibromopropane in the presence of sodium hydride (dispersed in mineral oil). The reaction is described as being carried out in dry dimethyl sulphoxide under nitrogen with stirring initially at room temperature, then at a temperature in the range 30 to 35° C. for 2 hours. This preparation is also reported in EP 191542 and GB 2127819.

The presence of dimethyl sulphoxide in the aqueous waste from these processes renders the waste ineligible for discharge to the chemical effluent drain of chemical production plants. The waste therefore has to be specially disposed of. This leads to high production costs and adverse environmental effects (more resources and energy are required to enable safe disposal of the aqueous waste). It is therefore desirable to find a process which does not require dimethyl sulphoxide.

Initially the reaction was attempted using toluene as the solvent. However, this course of action results in a new problem in that it leads to generation of a significant, delayed exotherm during addition to the reaction mixture of the arylacetonitrile. Such a process is not considered safe. The problem of exotherm generation does not arise when dimethyl sulphoxide is replaced with other water-miscible solvents, such as tetrahydrofuran. However, there is a significant loss of yield which can only be improved by partial distillation of the tetrahydrofuran and addition of a water-immiscible solvent, such as toluene, prior to extraction. Such a procedure has the disadvantages of requiring extra processing (increasing the cost) and of creating a tetrahydrofuran/toluene waste stream, both of which render it unsatisfactory. A similar process is described in WO93/13073 (page 180, Example N10) for producing 1-(4-trifluoromethoxyphenyl)cyclobutyl cyanide. In this process two water-miscible solvents, tetrahydrofuran and dimethylformamide, are used during the reaction, with the water-immiscible solvent ether being used for extraction of the product, to obtain a 61% yield. Again this has the disadvantage of requiring extra processing and producing a tetrahydrofuran/ether waste stream.

WO95/00489 describes a process for producing 1-(2-pyridyl)cyclopropyl cyanide This reaction was carried out in toluene using a 50% aqueous sodium hydroxide solution as the base. The base was added to a stirred mixture of 2-(2-pyridyl)acetonitrile, 1-bromo-2-chloroethane, benzyl-triethylammonium chloride and toluene at 25° C. The mixture was then heated at 70–75° C. for 2 hours. The product was extracted into ether and isolated in good yield (~85%). A disadvantage of this process is the presence of water in the initial reaction. This can lead to a rather high level of impurity formation. However, addition of an equivalent amount of a solid base at 25° C. (without the presence of water) would result in a significant delayed exotherm making such a reaction unsafe. Furthermore, it is well known that cyclobutyl rings, as described by the present invention, are considerably less facile to make than the cyclopropyl rings described in the above reference. Therefore it would not be expected that the above procedure would produce as good a yield of cyclobutyl material by using 1-bromo-2-chloropropane instead of 1-bromo-2-chloroethane. Additionally problems can arise from emulsion formation when water is present initially. This may lead to lower yields.

Surprisingly, we have found a process for the preparation of arylcyclobutyl cyanides whereby dimethyl sulphoxide can be excluded, delayed exotherms and mixed solvent waste streams avoided, and impurity formation kept to a minimum whilst still giving the desired product in good yield.

The present invention provides a process for the preparation of compounds of formula I

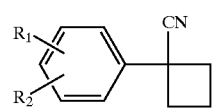

I in which $R_1$ and $R_2$, which may be the same or different, are H, halo, trifluoromethyl, an alkyl group containing 1 to 3 carbon atoms, an alkoxy or alkylthio group containing 1 to 3 carbon atoms, phenyl, or $R_1$ and $R_2$, together with the carbon atoms to which they are attached, form a second benzene ring which may be substituted by one or more substituents selected from halo, an alkyl group containing 1 to 4 carbon atoms, an alkoxy group containing 1 to 4 carbon atoms, or the substituents of the second benzene ring together with the two carbon atoms to which they are attached may form a further benzene ring;

said process comprising the reaction of a 1,3-dihalopropane, a compound of formula II

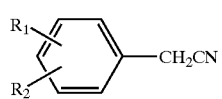

II in which $R_1$ and $R_2$ are as defined above, and a suspension of a base in a substantially dimethyl sulphoxide-free solvent at a temperature of at least 35° C.

A preferred process according to the present invention provides a process for the preparation of compounds of formula I as defined by formula III

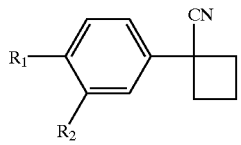

in which $R_1$ represents halo and $R_2$ represents hydrogen or halo; comprising the reaction of a 1,3-dihalopropane, a compound of formula II as defined by formula IV

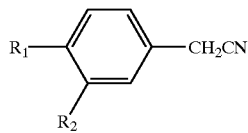

in which $R_1$ and $R_2$ are as defined above, and a suspension of a base in a substantially dimethyl sulphoxide-free solvent at a temperature of at least 35° C.

A more preferred process according to the present invention provides a process for the preparation of compounds of formula IV in which $R_1$ represents chloro and $R_2$ represents hydrogen or chloro comprising the reaction of a 1,3-dihalopropane, a compound of formula IV in which $R_1$ represents chloro and $R_2$ represents hydrogen or chloro, respectively, and a suspension of a base in a substantially dimethyl sulphoxide-free solvent at a temperature of at least 35° C.

The more preferred processes of the present invention provide a) a process for the preparation of 1-(4-chlorophenyl)cyclobutyl cyanide comprising the reaction of a 1,3-dihalopropane, 4-chlorophenylacetonitrile and a suspension of a base in a substantially dimethyl sulphoxide-free solvent at a temperature of at least 35° C.; and b) a process for the preparation of 1-(3,4-dichlorophenyl)cyclobutyl cyanide and a suspension of a base in a substantially dimethyl sulphoxide-free solvent at a temperature of at least 35° C.

A most preferred process of the present invention provides a process for the preparation of 1-(4-chlorophenyl) cyclobutyl cyanide comprising the reaction of a 1,3-dihalopropane, 4-chlorophenylacetonitrile and a suspension of a base in a substantially dimethyl sulphoxide-free solvent at a temperature of at least 35° C.

Preferably the process comprises the addition of a solution of a 1,3-dihalopropane and a compound of formula II in a substantially dimethyl sulphoxide-free solvent to a suspension of a base in a substantially dimethyl sulphoxide-free solvent at a temperature of at least 35° C.

The term "solvent" defines a water-immiscible liquid which is capable of keeping the 1,3-dihalopropane and the 4-chlorophenylacetonitrile in solution at the reaction temperature. The use of a water-immisicible liquid is advantageous as the work-up procedure is simplified and therefore process costs are reduced.

The term "substantially dimethyl sulphoxide-free" means that no more than 5% of dimethyl sulphoxide is present in the solvent, preferably no more than 2%, and most preferably there is a complete absence of dimethyl sulphoxide.

Suitably,the dimethyl sulphoxide-free solvent is a water immiscible organic liquid, preferably the liquid is non-polar. More preferably, the dimethyl sulphoxide-free solvent is a hydrocarbon such as toluene or petroleum ether. Most preferably the dimethyl sulphoxide-free solvent is toluene.

Preferably, the base is potassium hydroxide or sodium hydroxide. Preferably the amount of base present is at least 2 molar equivalents relative to the amount of the compound of formula II present. More preferably, the amount is in the range of 3.8 to 4.7 molar equivalents relative to the amount of the compound of formula II present.

The suspension of base is preferably maintained by agitation such as stirring, shaking, or bubbling an inert gas, such as nitrogen, through the solvent, but any other means of maintaining a suspension may also be used. Preferably it is a stirred suspension.

Preferably the reaction is carried out under an inert atmosphere such as nitrogen.

Preferably, there is a phase-transfer catalyst present in the suspension of the base. Suitably the phase transfer catalyst is a quaternary salt or a crown ether. Preferably the catalyst is selected from one of the following: butylpyridinium bromide, tetrabutylammonium bisulphate, benzyltriethylammonium bromide, benzyltriethylammonium chloride, benzyltrimethylammonium chloride, benzyltrimethylammonium fluoride, hexadecyltriethylammonium bromide, hexadecyltriethylphosphonium bromide, hexadecyltrimethylammonium bromide, hexadecyltrimethylammonium chloride, dibutyldimethylammonium chloride, decyltriethylammonium bromide, hexadecyltributylphosphonium bromide, heptylpyridinium bromide, hexadecyltributylphosphonium chloride, hexyltriethylammonium bromide, dodecylpyridinium bromide, dodecyltriethylammonium bromide, methyltrinonylammonium chloride, methyltriphenylammonium bromide, tetrabutylammonium bromide or bisulphate, tetrabutylammonium chloride, tetrabutylammonium cyanide, tetrabutylammonium fluoride, tetrabutylammonium iodide, tetrabutylammonium hydroxide, tetrabutylphosphonium chloride, tricaprylylmethylammonium chloride, tetraethylammonium chloride, tetramethylammonium bromide, trioctylethylphosphonium bromide, trioctylmethylammonium chloride, trioctylpropylammonium chloride, tetrapropylammonium bromide, tetraphenylarsonium chloride, tetraphenylphosphonium bromide, tetraphenylphosphonium chloride, benzyltrimethylammonium hydroxide, 18-crown-6, dibenzo-18-crown-6, dicyclohexyl-18-crown-6 or mixtures thereof. More preferably the phase transfer catalyst is a quaternary ammonium salt or a crown ether. Most preferably, the phase-transfer catalyst is tetra-n-butylammonium bromide, tetra-n-butylammonium hydrogen sulphate, or tetra-n-butylammonium iodide.

Preferably the amount of phase-transer catalyst present is in the range of 0.01 to 0.2 molar equivalents relative to the amount of the compound of formula II present. More preferably the amount is in the range of 0.05 to 0.15 molar equivalents relative to the amount of the compound of formula II present.

Preferably, the temperature is in the range 35–80° C., more preferably in the range 35.1–69° C., most preferably in the range 40–60° C.

Preferably, water is added to aid stirring when the addition is 60–85% complete, more preferably 75% complete. Suitably the volume of water added is in the range of 0 to 5.0 parts by weight relative to the weight of the compound of formula II present. Preferably the volume of water added is in the range of 0 to 1.0 parts of weight relative to the weight of the compound of formula II present. More preferably the volume of water added is on the range of 0.7 to 0.9 parts by weight relative to the weight of the compound of formula II present.

Preferably, the reaction is quenched by the addition of water.

Preferably, the reaction is carried out at atmospheric pressure.

Suitably the 1,3-dihalopropane is 1,3-dibromopropane, 1,3-dichloropropane or 1-bromo-3-chloropropane. Preferably the 1,3-dihalopropane is 1,3-dibromopropane.

Suitably the amount of 1,3-dihalopropane used is in the range of 0.8 to 1.5 molar equivalents relative to the amount of the compound of formula II present. Preferably the amount of 1,3-dihalopropane used is in the range of 0.9 to 1.2 molar equivalents relative to the amount of the compound of formula II present. Most preferably the amount of 1,3-dihalopropane used is in the range 1.0 to 1.05 molar equivalents relative to the amount of the compound of formula II present.

When compounds of formula I are prepared by the process which comprises the present invention, there can be observed a significant financial saving both in terms of raw materials and disposal of the aqueous waste when compared to the known process carried out in dimethyl sulphoxide. Also, there is additional benefit to the environment because it obviates the need to dispose of waste dimethyl sulphoxide. In addition certain impurities which arise from the oxidising nature of dimethyl sulphoxide are eliminated leading to simplified work-up procedures and a purer product.

A further advantage of the present invention is that it may avoid the need for isolation of 1-(4-chlorophenyl)cyclobutyl cyanide when it is desired to obtain sibutramine. Instead it may be possible to use the toluene solution of 1-(4-chlorophenyl)cyclobutanecarbonitrile immediately in the reaction described in GB2098602A, incorporated herein by reference.

of each of these Examples was characterised by one or more of the following procedures: gas-liquid chromatography; high performance liquid chromatography; elemental analysis; nuclear magnetic resonance spectroscopy and infrared spectroscopy.

EXAMPLES

The following procedure was carried out under the conditions listed in Table 1 to obtain compounds of formula I.

75% of a mixture (m) of 4-chlorophenylacetonitrile (II) (x g) and 1,3-dibromopropane (y g) in toluene (z ml) was added to a stirred mixture of a base (a g) and a catalyst (b g) in toluene (c ml) over 1.5 hours at a temperature of d° C. Water (e ml) was added, keeping the temperature at d° C. The remaining 25% of the mixture (m) was then added over 30 minutes at d° C., and the mixture stirred for 2.5 hours at f° C. The reaction was then quenched by addition of water (254 ml) over 15 minutes at d° C., and the mixture stirred for 20 minutes.

The organic phase was separated and stirred with water (354 ml) and caustic soda (76 g) at f° C. for 15 minutes, then allowed to settle. The organic layer was separated, then stirred at f° C. with water (300 ml) and concentrated hydrochloric acid (20 ml), the aqueous layer having a pH of 3 or less. The organic layer was separated, then stirred with water (300 ml) at f° C. for 15 minutes and the organic layer separated. This was repeated until the aqueous layer had a pH between 6 and 8.

The solvent was removed in vacuo at 90° C., and the residual oil was distilled at 1.33 to 2.66 mbar under high vacuum to yield in the appropriate fractions a compound of formula I, yield g %.

TABLE 1

Examples 1–10

| Mass of compound II | Mass of dibromo-propane | Catalyst | Mass of catalyst | Mass of base (powdered potassium hydroxide) | Temperature (d ° C.) and | Toluene charge | | Water charged @ 75% of addition | Yield |
|---|---|---|---|---|---|---|---|---|---|
| (x g) | (y g) | | (b g) | (a g) | (f ° C.) | (z ml) | (c ml) | (e ml) | (g %) |
| 75 | 105 | TBAB | 11.8 | 132 | 40 | 66 | 360 | 60 | 53.2 |
| 75 | 105 | TBAB | 11.8 | 132 | 40 | 66 | 360 | 60 | 57.3 |
| 75 | 105 | TBAB | 11.8 | 132 | 40 | 66 | 360 | 60 | 61.4 |
| 75 | 105 | TBAB | 11.8 | 132 | 40 | 66 | 360 | 0 | 56.5 |
| 75 | 105 | TBAB | 11.8 | 132 | 60 | 66 | 360 | 60 | 57.5 |
| 75 | 105 | TBAB | 11.8 | 132 | 60 | 66 | 360 | 60 | 63.2 |
| 75 | 105 | TBAHS | 12.4 | 132 | 40 | 66 | 360 | 0 | 57.8 |
| 75 | 105 | TBAHS | 12.4 | 132 | 40 | 66 | 360 | 0 | 62.6 |
| 75 | 105 | TBAHS | 12.4 | 132 | 60 | 66 | 360 | 60 | 61.3 |
| 75 | 105 | TBAHS | 12.4 | 132 | 60 | 66 | 360 | 60 | 57.9 |

TBAB means tetra-n-butylammonium bromide;
TBAHS means tetra-n-butylammonium hydrogen sulphate.
Temperatures d ° C. and f ° C. are the same for Examples 1–10.

In one embodiment of the present invention, the process comprises the addition of a solution of 1,3-dibromopropane and 4-chlorophenylacetonitrile in toluene to a stirred suspension of powdered potassium hydroxide with tetra-n-butylammonium bromide in toluene at a temperature in the range 35–80° C., preferably in the range 35.1–69° C., more preferably in the range 40–60° C. Water is added after 60–85% completion of the addition. The reaction is quenched by the addition of water.

The invention is illustrated by the following Examples which are given by way of example only. The final product The same procedure was carried out for Comparative Examples 11–15, except that tetrahydrofuran was used in place of toluene. The temperature (d° C.) for the initial reaction was the temperature used in the original process with dimethylsulphoxide, viz room temperature (20–25° C.), rising to 30–35° C. (f° C.) for the final stir (for 1.5 hours not 2.5 hours) and separation steps. The only exception was Example 15 where the separation steps were carried out at 20–25° C. (d° C.) instead of 30–35° C. (f° C.). The other conditions and yields for these Examples are listed in Table 2. It can be seen that the yields are inferior to the results obtained using toluene at a temperature of at least 35° C.

The same procedure was carried out for Comparative Examples 16–17, except that a mixture of dimethyl sulphoxide and toluene was used in place of toluene. The temperature (d° C.) for the initial reaction was the temperature used in the original process with dimethylsulphoxide, viz room temperature (20–25° C.), rising to 30–35° C. (f° C.) for the final stir (for 1.5 hours not 2.5 hours) and separation steps. The other conditions and yields for these Examples are listed in Table 3. It can be seen that the yields are comparable to the results obtained using toluene at a temperature of at least 35° C. However, as mentioned previously there is the disadvantage of waste dimethyl sulphoxide.

TABLE 2

Comparative Examples 11–15

| Mass of compound II (x g) | Mass of dibromo-propane (y g) | Catalyst | Mass of catalyst (b g) | Mass of potassium hydroxide (a g) | Temperature (d ° C., f ° C.) | Tetrahydrofuran charge (z + c) (including all washes) (ml) | Water charged @ 75% of addition (e ml) | Yield (g %) |
|---|---|---|---|---|---|---|---|---|
| 75 | 105 | TBAB | 11.8 | 132 | 20–25, 30–35 | 640 | 60 | 29.4 |
| 75 | 105 | TBAB | 11.8 | 132 | 20–25, 30–35 | 640 | 0 | 36.4 |
| 75 | 105 | TBAB | 11.8 | 132 | 20–25, 30–35 | 790 | 0 | 20.3 |
| 75 | 105 | TBAB | 11.8 | 132 | 20–25, 30–35 | 640 | 0 | 44.1 |
| 75 | 105 | TBAB | 11.8 | 132 | 20–25, 30–35 | 840 | 0 | 35.3 |

TBAB means tetra-n-butylammonium bromide;
TBAHS means tetra-n-butylammonium hydrogen sulphate.

TABLE 3

Comparative Examples 16–17

| Mass of compound II (x g) | Mass of dibromo-propane (y g) | Catalyst | Mass of catalyst (b g) | Mass of potassium hydroxide (a g) | Temperature (d ° C., f ° C.) | DMSO/toluene charge (z + c) (including all washes) (ml) | Water charged @ 75% of addition (e ml) | Yield (g %) |
|---|---|---|---|---|---|---|---|---|
| 150 | 209.6 | TBAB | 22.4 | 264 | 20–25, 30–35 | 120/1080 | 120 | 62 |
| 75 | 104.8 | TBAB | 11.2 | 132 | 20–25, 30–35 | 60/345 | 60 | 55 |

TBAB means tetra-n-butylammonium bromide;
TBAHS means tetra-n-butylammonium hydrogen sulphate;
DMSO means dimethyl sulphoxide.

Example 18

75% of a mixture (m) of 1-(3,4-dichlorophenyl) acetonitrile (92.1 g) and 1,3-dibromopropane (105 g) in toluene (66 ml) is added to a stirred mixture of powdered potassium hydroxide (132 g) and tetra-n-butylammonium bromide (11.8 g) in toluene (360 ml) over 1.5 hours at a temperature of 60° C. Water (60 ml) is added, keeping the temperature at 60° C. The remaining 25% of the mixture (m) is then added over 30 minutes at 60° C., and the mixture stirred for 2.5 hours at 60° C. The reaction is then quenched by addition of water (254 ml) over 15 minutes at 60° C., and the mixture stirred for 20 minutes. The organic phase is separated and stirred with water (354 ml) and caustic soda (76 g) at 60° C. for 15 minutes, then allowed to settle. The organic layer is separated, then stirred at 60° C. with water (300 ml) and concentrated hydrochloric acid (20 ml), the aqueous layer having a pH of 3 or less. The organic layer is separated, then stirred with water (300 ml) at 60° C. for 15 minutes and the organic layer separated. This is repeated until the aqueous layer has a pH between 6 and 8. The solvent is removed in vacuo at 90° C., and the residual oil is distilled at 1.33 to 2.66 mbar under high vacuum to yield in the appropriate fractions of 1-(3,4-dichlorophenyl) cyclobutyl cyanide.

What is claimed is:

1. A process for the preparation of compounds of formula I

I in which $R_1$ and $R_2$, which may be the same or different, are H, halo, trifluoromethyl, an alkyl group containing 1 to 3 carbon atoms, an alkoxy or alkylthio group containing 1 to 3 carbon atoms, phenyl, or $R_1$ and $R_2$, together with the carbon atoms to which they are attached, form a second benzene ring which may be substituted by one or more substituents selected from halo, an alkyl group containing 1 to 4 carbon atoms, an alkoxy group containing 1 to 4 carbon atoms, or the substituents of the second benzene ring together with the two carbon atoms to which they are attached may form a further benzene ring;

said process comprising the reaction of a 1,3-dihalopropane, a compound of formula II

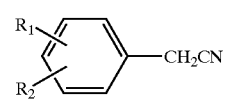

II and a suspension of a base in a substantially dimethyl sulphoxide-free solvent at a temperature of at least 35° C.

2. A process as claimed in claim 1 comprising the addition of a solution of a 1,3-dihalopropane and a compound of formula II in a substantially dimethyl sulphoxide-free solvent to a suspension of a base in a substantially dimethyl sulphoxide-free solvent at a temperature of at least 35° C.

3. A process as claimed in claim 2 in which there is a phase-transfer catalyst present in the suspension of the base.

4. A process as claimed in claim 3 in which the phrase-transfer catalyst is tetra-n-butylammonium bromide, tetra-n-butylammonium hydrogen sulphate, tetra-n-butylammonium iodide or a crown ether.

5. A process as claimed in claim 1 in which the dimethyl sulphoxide-free solvent is toluene.

6. A process as claimed in claim 1 in which the base is potassium hydroxide or sodium hydroxide.

7. A process as claimed in claim 1 in which the temperature is in the range 35–80° C.

8. A process as claimed in claim 1 claim in which the compound of formula II is 4-chlorophenylacetonitrile.

9. A process as claimed in claim 1 in which the compound of formula II is 3,4-dichlorophenylacetonitrile.

10. A process as claimed in claim 2 in which water is added after 60–85% of the addition is complete.

* * * * *